(12) United States Patent
Hu et al.

(10) Patent No.: US 12,036,750 B2
(45) Date of Patent: Jul. 16, 2024

(54) DISPOSABLE BIOPROCESS BAG, MANUFACTURING METHOD THEREFOR, HOT-MELT ANNULAR WELDING MACHINE

(71) Applicant: ZHEJIANG JINYISHENGSHI BIOENGINEERING CO., LTD., Huzhou (CN)

(72) Inventors: Fulin Hu, Huzhou (CN); Shiping Yuan, Huzhou (CN); Jinpei Song, Huzhou (CN); Wei Han, Huzhou (CN)

(73) Assignee: ZHEJIANG JINYISHENGSHI BIOENGINEERING CO., LTD., Huzhou (CN)

( * ) Notice: Subject to any disclaimer, the term of this patent is extended or adjusted under 35 U.S.C. 154(b) by 700 days.

(21) Appl. No.: 17/262,712

(22) PCT Filed: Jul. 23, 2019

(86) PCT No.: PCT/CN2019/097183
§ 371 (c)(1),
(2) Date: Jan. 23, 2021

(87) PCT Pub. No.: WO2020/020116
PCT Pub. Date: Jan. 30, 2020

(65) Prior Publication Data
US 2021/0229373 A1    Jul. 29, 2021

(30) Foreign Application Priority Data

Jul. 23, 2018    (CN) .......................... 201810812327.7

(51) Int. Cl.
*B29C 65/00*    (2006.01)
*B29C 65/48*    (2006.01)
(Continued)

(52) U.S. Cl.
CPC ...... *B29C 66/8511* (2013.01); *B29C 65/4815* (2013.01); *B31B 70/20* (2017.08);
(Continued)

(58) Field of Classification Search
CPC . B29C 65/02; B29C 65/4815; B29C 66/8511; C12M 23/14; C12M 23/28;
(Continued)

(56) References Cited

U.S. PATENT DOCUMENTS 3,444,732 A * 5/1969 Mckinley ................ B29C 65/18
156/64
2021/0229373 A1* 7/2021 Hu .......................... B31B 70/20

FOREIGN PATENT DOCUMENTS

| CN | 102529170 A | 7/2012 |
| CN | 102744878 A | 10/2012 |
| CN | 108018204 A | 5/2018 |

OTHER PUBLICATIONS

Translation of ISR of PCT/CN2019/097183.*
(Continued)

*Primary Examiner* — Sonya M Sengupta
(74) *Attorney, Agent, or Firm* — NZ CARR LAW OFFICE

(57) ABSTRACT

The present invention provides a disposable bioprocess bag, a manufacturing method therefor and a hot-melt annular welding machine, relating to the technical field of biopharmaceutics. The manufacturing method comprises: preparing a first cropping template to a fourth cropping template according to a top, an upper portion, a lower portion and a bottom of a bioreactor; cropping a raw material film according to the first cropping template to the fourth cropping template to obtain a first membrane material to a fourth membrane material, wherein the fourth membrane material directly serves as a rounded bottom; welding at least two
(Continued)

pockets on the first membrane material to obtain a rounded top; welding the second membrane material to obtain a cylindrical upper portion; welding the third membrane material to obtain a lower portion in the shape of an inverted rounded truncated cone; and welding, using a hot-melt annular welding machine, the rounded top, the cylindrical upper part, the lower portion in the shape of an inverted rounded truncated cone and the rounded bottom, to obtain a disposable bioprocess bag. According to the present invention, the physical properties of the welded edge of the disposable bioprocess bag are improved, and the fit of the disposable bioprocess bag to the bioreactor are also enhanced.

16 Claims, 4 Drawing Sheets

(51) Int. Cl.
*B31B 70/20* (2017.01)
*B31B 70/64* (2017.01)
*B31B 150/00* (2017.01)
*C12M 1/00* (2006.01)

(52) U.S. Cl.
CPC .............. *B31B 70/64* (2017.08); *C12M 23/14* (2013.01); *C12M 23/28* (2013.01); *B31B 2150/00* (2017.08)

(58) Field of Classification Search
CPC .......... B31B 2150/00; B31B 2150/002; B31B 2150/003; B31B 2160/20; B31B 2160/30; B31B 2241/00; B31B 70/04; B31B 70/14; B31B 70/20; B31B 70/64; B31B 70/642; B31B 70/84
See application file for complete search history.

(56) References Cited

OTHER PUBLICATIONS

English translation of CN102744878.*
English translation of CN108018204.*
English translation of CN102529170.*
China National Intellectual Property Administration, International Search Report, for PCT/CN2019/097183, mail date Oct. 25, 2019.

* cited by examiner

DISPOSABLE BIOPROCESS BAG, MANUFACTURING METHOD THEREFOR, HOT-MELT ANNULAR WELDING MACHINE

FIELD OF THE INVENTION

The present invention relates to biopharmaceutical technical field, and in particular, the present invention relates to a single-use bioprocessing bag and manufacturing method thereof, and a hot-melt ring welding machine.

BACKGROUND OF THE INVENTION

With the continuous development of biopharmaceutical technology, single-use systems (Single-use Systems, referred to simply as SUS) have become more and more widely used. Single-use bioprocessing bags, as supporting supplies for single-use systems, still have many deficiencies in actual production process and in practical applications.

The existing single-use bioprocessing bags undergo multiple straight-line welding during the production process, and there are many overlapping parts of welding edges, and physical properties of the multiple overlapping parts are significantly reduced, which increases risks of rupture of the single-use bioprocessing bags and leakage of culture liquid in the bags. At the same time, in actual application process, the poor conformability between the existing single-use bioprocessing bags and bioreactors will cause flow field of the culture liquid inside a culture system to deviate from ideal flow field confirmed during design, which affects the final cell culture effect.

SUMMARY OF THE INVENTION

The present invention provides a single-use bioprocessing bag and a manufacturing method thereof, and a hot-melt ring welding machine, which can improve physical properties of a welding edge of the single-use bioprocessing bag, and at the same time improve the conformability between the single-use bioprocessing bag and a bioreactor.

In the first aspect, the present invention provides a manufacturing method of single-use bioprocessing bag, wherein:
the single-use bioprocessing bag is used to be placed in a bioreactor, with an upper top of the bioreactor being circular, an upper part of the bioreactor being cylindrical, a lower part of the bioreactor being inverted truncated cone shape, and a lower bottom of the bioreactor being circular, the single-use bioprocessing bag comprises a circular upper top, a cylindrical upper part, a lower part of an inverted truncated cone, and a circular lower bottom, with the circular upper top having at least two bag openings;
the manufacturing method comprises:
a first cutting template, a second cutting template, a third cutting template, and a fourth cutting template being made respectively according to the upper top, the upper part, the lower part and the lower bottom of the bioreactor;
cutting a raw film material according to the first cutting template to obtain a first film material, cutting the raw film material according to the second cutting template to obtain a second film material, cutting the raw film material according to the third cutting template to obtain a third film material, cutting the raw film material according to the fourth cutting template to obtain a fourth film material, and the fourth film material directly serving as the circular lower bottom;
welding the at least two bag openings on the first film material to obtain the circular upper top;
welding the second film material to obtain the cylindrical upper part;
welding the third film material to obtain the inverted truncated cone lower part;
using a hot-melt ring welding machine to weld the circular upper top, the cylindrical upper part, the inverted truncated cone lower part, and the circular lower bottom to obtain the single-use bioprocessing bag, wherein the hot-melt ring welding machine is used to weld an annular welding edge.

Optionally, the error between the size of the first film material and the size of the first cutting template is less than or equal to 2 mm, the error between the size of the second film material and the size of the second cutting template is less than or equal to 2 mm, the error between the size of the third film material and the size of the third cutting template is less than or equal to 2 mm, and the error between the size of the fourth film material and the size of the fourth cutting template is less than or equal to 2 mm.

Optionally, when cutting the raw film material, two layers of the raw film material at the most are cut each time.

Optionally, when welding the at least two bag openings on the first film material, the processing parameters are as following:
the air pressure is 0.5 MPa, the temperature of the upper mold is 110° C.±2° C., the temperature of the lower mold is 80° C.±2° C., the gap between the upper mold and the lower mold is 1.5 mm, the welding time is 6 s~8 s, and the width of the welding edge is 8 mm.

Optionally, when welding the at least two bag openings on the first film material, a layer of high temperature cloth is placed on a non-welding surface of the first film material.

Optionally, when welding the second film material, the processing parameters are as following:
the air pressure is 0.6 MPa, the temperature of the upper mold is 135° C.±2° C., the temperature of the lower mold is 90° C.±2° C., the gap between the upper mold and the lower mold is 0.6 mm, the welding time is 6 s~9 s, the width of the welding edge is 10 mm, and the thickness of the welding edge is 0.6 mm±0.1 mm.

Optionally, when welding the third film material, the processing parameters are as following:
the air pressure is 0.6 MPa, the temperature of the upper mold is 135° C.±2° C., the temperature of the lower mold is 90° C.±2° C., the gap between the upper mold and the lower mold is 0.6 mm, the welding time is 6 s~9 s, the width of the welding edge is 10 mm, and the thickness of the welding edge is 0.6 mm±0.1 mm.

Optionally, when using the hot-melt ring welding machine to perform welding of the circular upper top, the cylindrical upper part, the inverted truncated cone lower part, and the circular lower bottom, the processing parameters are as following:
the air pressure is 0.6 MPa, the temperature of the upper mold is 135° C.±2, the welding time is 50 s~55 s, and the width of the welding edge is 10 mm. In this embodiment, the lower mold is not heated.

Optionally, the manufacturing method further comprises: during the process of using the hot-melt ring welding machine to perform welding of the circular upper top, the cylindrical upper part, the inverted truncated cone lower part, and the circular lower bottom, the upper mold and the lower mold of the hot-melt ring welding machine are changed according to the diameter of the circular upper top and the diameter of the circular lower bottom, respectively.

Optionally, the manufacturing method further comprises: after obtaining the single-use bioprocessing bag, performing an air tightness test on the single-use bioprocessing bag using a pressure drop method.

Optionally, in the pressure drop method, the parameters of a pressure holding process are as following:

the ambient temperature is 26° C.±2° C. in summer time, 20° C.±2° C. in winter time, the humidity is 40%-60%, and a pressure holding time is 48 h;

when the volume of the single-use bioprocessing bag is 5 L, the holding pressure is 4 kPa; when the volume of the single-use bioprocessing bag is 50 L, the holding pressure is 2 kPa; when the volume of the single-use bioprocessing bag is 300 L, the holding pressure is 0.6 kPa; and when the volume of the single-use bioprocessing bag is 1200 L, the holding pressure is 0.3 kPa.

In the second aspect, the present invention provides a single-use bioprocessing bag made with any of the above manufacturing methods of a single-use bioprocessing bag.

In the third aspect, the present invention provides a hot-melt ring welding machine, comprising a base, a support, an upper mold, a lower mold, a cylinder, and a screw guide rail, wherein the lower mold is detachably connected to the base, the support is fixed to one end of the base, the screw guide rail is fixed on the support, the cylinder is fixed on the screw guide rail, the upper mold is detachably connected to the bottom of the piston of the cylinder, the upper mold is of an arc-shaped piece, the lower mold is a hollow cylinder, the upper mold has a built-in heating module, and the lower mold is able to rotate about its axial direction at any angle between 0 and 360°.

Optionally, a silicone plate is laid on the upper surface of the lower mold.

Optionally, the thickness of the silicone plate is 2 mm.

Optionally, the hot-melt ring welding machine comprises two cylinders, in the vertical direction the position of the screw guide rail overlaps with the position of the symmetry axis of the upper mold, and the two cylinders are symmetrically arranged with respect to the symmetry axis of the upper mold.

The present invention provides a single-use bioprocessing bag and manufacturing method thereof, and a hot-melt ring welding machine. On one hand, because during the process of manufacturing the single-use bioprocessing bag using the above manufacturing method of the single-use bioprocessing bag, at least two bag openings are welded on the first film material to obtain the circular upper top, the second film material is welded to obtain the cylindrical upper part, the third film material is welded to obtain the inverted truncated cone lower part, and the hot-melt ring welding machine is used to weld the circular upper top, the cylindrical upper part, the inverted truncated cone lower part, and the circular lower bottom, so as to obtain the single-use bioprocessing bag, there are fewer welding times, fewer welding edges, and smaller overlapping parts of the welding edges during the manufacturing process of the single-use bioprocessing bag, which can improve the physical properties of the welding edge of the single-use bioprocessing bag and reduce the risk of rupture of the single-use bioprocessing bag and the leakage of the culture liquid in the bag. On the other hand, because the first film material, the second film material, the third film material and the fourth film material are all made by cutting the raw film material according to the first cutting template, the second cutting template, the third cutting template and the fourth-cutting template that are made based on the size and shape of the bioreactor, the conformability between the single-use bioprocessing bag and the bioreactor can be improved, and the problem that the flow field shape of the culture liquid inside a culture system deviates from ideal flow field shape confirmed during design is solved, thus helping to improve the final cell culture effect.

BRIEF DESCRIPTION OF THE DRAWINGS

The following drawings are used to illustrate embodiments more clearly, and should not be construed as limiting the protection scope of the present invention.

DETAILED DESCRIPTION OF THE INVENTION

In order to illustrate technical solutions and advantages of the present invention more clearly, the technical solutions of the present invention will be described clearly and completely in conjunction with the accompanying drawings. The described embodiments are part of embodiments of the present invention, rather than all of them, and should not be construed as limiting the protection scope of the present invention.

It should be noted that, in the case of no conflict, technical features in the embodiments of the present invention can be combined with each other.

Figure 1:
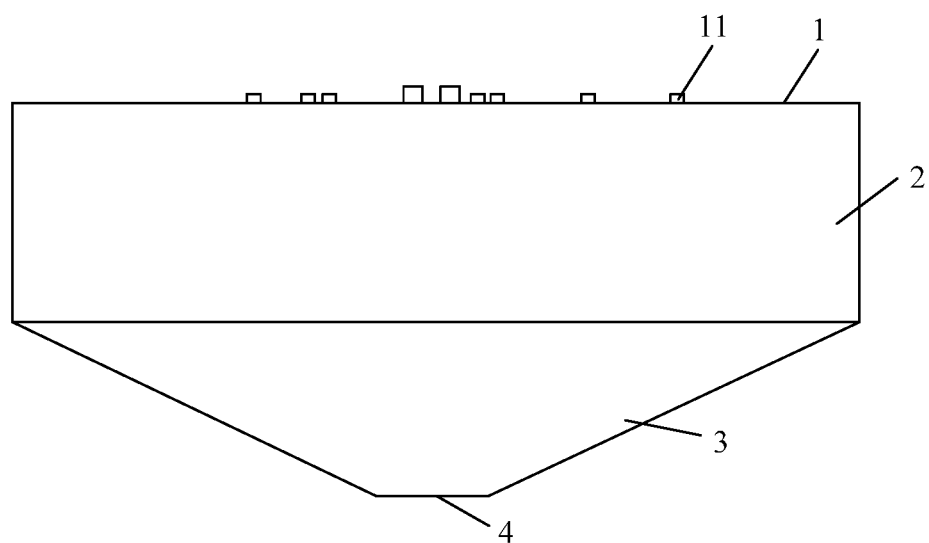
FIG. 1 shows a schematic diagram of the structure of a single-use bioprocessing bag.

A single-use bioprocessing bag is used to be placed in a bioreactor, wherein the upper top (that is, the top of the upper part) of the bioreactor is circular, the upper part of the bioreactor is cylindrical, the lower part of the bioreactor is of inverted truncated cone shape, and the lower bottom (that is, the bottom of the lower part) of the bioreactor is circular, as shown in FIG. 1. FIG. 1 is a schematic diagram of the structure of the single-use bioprocessing bag, wherein the single-use bioprocessing bag comprises a circular upper top 1, a cylindrical upper part 2, an inverted truncated cone lower part 3, and a circular lower bottom 4, and the circular upper top 1 has at least two bag openings 11.

Figure 2:
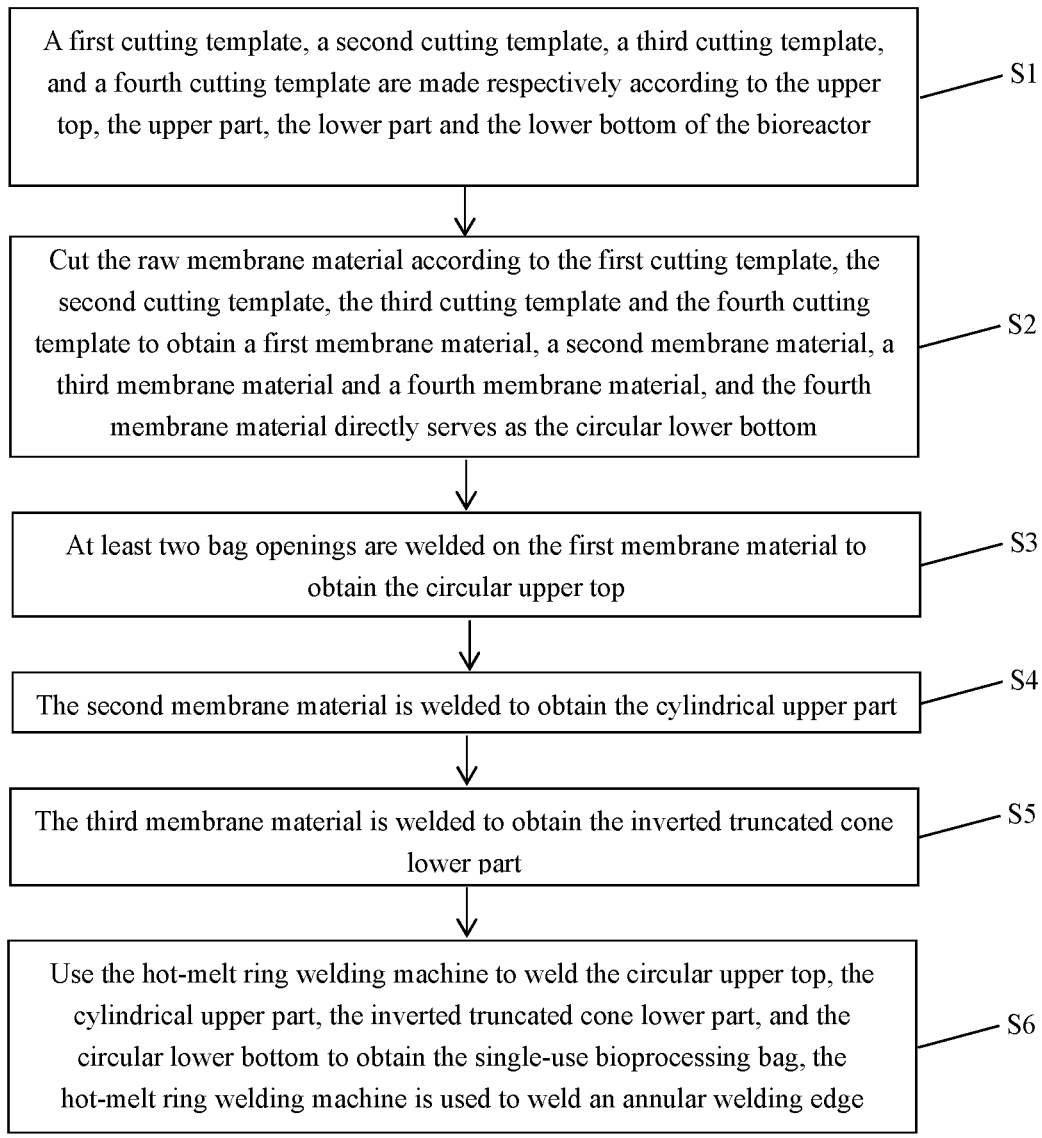
FIG. 2 shows a flow chart of a manufacturing method of a single-use bioprocessing bag.

As shown in FIG. 2, FIG. 2 is a flow chart of a manufacturing method of the single-use bioprocessing bag, and the manufacturing method of the single-use bioprocessing bag comprises:

Step S1: A first cutting template, a second cutting template, a third cutting template, and a fourth cutting template are obtained respectively according to the upper top, the upper part, the lower part, and the lower bottom of the bioreactor.

Figure 3:
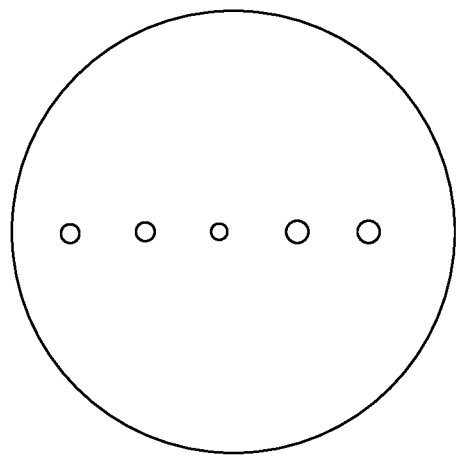
FIG. 3 shows a schematic diagram of a structure of the first cutting template.
Figure 4:
FIG. 4 shows a schematic diagram of a structure of the second cutting template.
Figure 5:
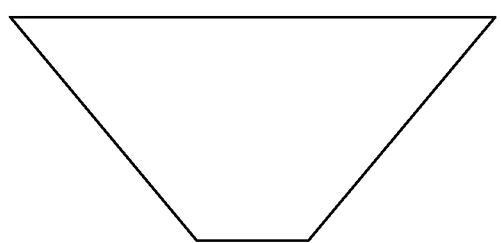
FIG. 5 shows a schematic diagram of a structure of the third cutting template.
Figure 6:
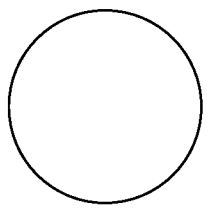
FIG. 6 shows a schematic diagram of a structure of the fourth cutting template.

Specifically, the first cutting template corresponds to the shape and size of the upper top, as shown in FIG. 3, which is a schematic diagram of the structure of the first cutting template. The shape of the first cutting template is circular, its circumference is the circumference of the upper top, and it has openings corresponding to at least two bag openings. The second cutting template corresponds to the unfolded shape and size of inner wall of the upper part, as shown in FIG. 4. FIG. 4 is a schematic diagram of the structure of the second cutting template, wherein the shape of the second cutting template is rectangular, the length of its two opposite sides is the circumference of the cross section of the upper part's inner wall, and the length of the other two opposite sides is the height of the upper part. The third cutting template corresponds to the unfolded shape and size of inner wall of the lower part, as shown in FIG. 5. FIG. 5 is a schematic diagram of the structure of the third cutting template, wherein the shape of the third cutting template is inverted trapezoid, the length of the longer bottom side is the circumference of the cross section of the upper part's inner wall, and the length of the shorter bottom side is the circumference of the lower bottom. The fourth cutting template corresponds to the shape and size of the lower bottom, as shown in FIG. 6. FIG. 6 is a schematic diagram of the structure of the fourth cutting template, wherein the shape of the fourth cutting template is circular, and its circumference is the circumference of the lower bottom.

It should be noted that FIG. 1 to FIG. 6 only show shapes and do not represent actual size relationships.

Step S2: Cutting the raw film material according to the first cutting template, the second cutting template, the third cutting template and the fourth cutting template to obtain a first film material, a second film material, a third film material and a fourth film material, and the fourth film material directly serves as the circular lower bottom.

"Cutting the raw film material according to the first cutting template, the second cutting template, the third cutting template and the fourth cutting template to obtain the first film material, the second film material, the third film material and the fourth film material" means that the raw film material is cut according to the first cutting template to obtain the first film material, the raw film material is cut according to the second cutting template to obtain the second film material, the raw film material is cut according to the third cutting template to obtain the third film material, and the raw film material is cut according to the fourth cutting template to obtain the fourth film material.

Wherein, the error between the size of the first film material and the size of the first cutting template is less than or equal to 2 mm, the error between the size of the second film material and the size of the second cutting template is less than or equal to 2 mm, the error between the size of the third film material and the size of the third cutting template is less than or equal to 2 mm, and the error between the size of the fourth film material and the size of the fourth cutting template is less than or equal to 2 mm, so as to make the single-use bioprocessing bag and the bioreactor fit with each other better.

Further, in order to ensure that the above errors are less than or equal to 2 mm, when cutting the raw film material according to the size and shape of the bioreactor, only two layers of the raw film material at the most (such as one or two layers) are cut each time.

For example, the above-mentioned raw film material is a special film suitable for cell culture. During the cutting process, firstly the raw film material is spread on the worktable, and then cut according to the cutting template (a collective name of the first cutting template, the second cutting template, the third cutting template and the fourth cutting template). If an automatic cutting knife is used to cut, it is ensured that the cutting templates or ruler cannot be displaced, so as to minimize the size error caused during the cutting process.

Step S3: The at least two bag openings are welded on the first film material to obtain the circular upper top.

Wherein, those that are welded on the surface of the first film material and can be connected to a pipeline are collectively referred to as the bag openings. The above-mentioned bag openings may be a sampling port, an air outlet, a liquid outlet, a sensor interface, a spare pipe, an air inlet, a liquid inlet, etc. A hot melt liquid bag opening welding machine can be used to weld the at least two bag openings on the first film material.

The inventors found that in the process of welding film materials using various hot-melt welding machines, the air pressure (that is, the downward pressure exerted by the cylinder of the hot-melt welding machine on the upper mold), the temperature of the upper mold, the temperature of the lower mold, the gap between the upper mold and the lower mold, the welding time, and the width of the welding edges, among other processing parameters, will all affect the welding effect. More specifically, it is as below:

Too low air pressure, too low temperature of the upper mold, too low temperature of the lower mold, too large gap between the upper mold and the lower mold, and too short welding time will cause that the welding edges cannot be uniformly and fully fused and affect the welding strength. Excessive air pressure, too high temperature of the upper mold, too high temperature of the lower mold, too small gap between the upper mold and the lower mold, and too long welding time will damage the inner surface structure layer of the film material, which will lead to the decrease of physical properties of the welding edge and the destruction of oxygen barrier layer. Too narrow welding edge will affect welding strength, and too wide welding edge will cause waste of the film material.

Based on the above, when welding the at least two bag openings on the first film material, the processing parameters are as the following: the air pressure is 0.5 MPa, the temperature of the upper mold is 110° C.±2° C., the temperature of the lower mold is 80° C.±2° C., the gap between the upper mold and the lower mold is 1.5 mm, the welding time is 6 s~8 s, and the width of the welding edge is 8 mm.

For example, the specific way of welding the at least two bag openings on the first film material is as follows: adjusting the gap between the upper mold and the lower mold to 1.5 mm, using the upper mold heating system in the hot-melt welding machine to heat up the upper mold to 110° C.±2° C., then the upper mold being given a downward pressure of 0.5 MPa through the air cylinder so that the upper mold and the lower mold squeeze the first film material and the bag openings at a fixed pressure, and the welding time being 6 s~8 s to make the welding surfaces fully fused after heating, so as to ensure that the sealing performance and heat sealing strength of the welding edges meet the requirements.

Optionally, when welding at least two bag openings on the first film material, a layer of high temperature cloth is placed on the non-welding surface of the first film material, to avoid destroying the non-welding surface of the first film material during the welding.

Step S4: The second film material is welded to obtain the cylindrical upper part.

A hot-melt straight-line welding machine can be used to weld the second film material to obtain the cylindrical upper part.

Optionally, when welding the second film material, the processing parameters are as the following: the air pressure is 0.6 MPa, the temperature of the upper mold is 135° C.±2° C., the temperature of the lower mold is 90° C.±2° C., the gap between the upper mold and the lower mold is 0.6 mm, the welding time is 6 s~9 s, the width of the welding edge is 10 mm, and the thickness of the welding edge is 0.6 mm±0.1 mm.

The reasons for selecting the above processing parameters and the specific welding way in S4 is similar to the specific contents in S3, and will not be repeated here.

Step S5: The third film material is welded to obtain the inverted truncated cone lower part.

In the embodiment of the present invention, a hot-melt straight line welding machine can be used to weld the third film material to obtain the inverted truncated cone lower part.

Optionally, when welding the third film material, the processing parameters are as the following: the air pressure is 0.6 MPa, the temperature of the upper mold is 135° C.±2° C., the temperature of the lower mold is 90° C.±2° C., the gap between the upper mold and the lower mold is 0.6 mm, the welding time is 6 s~9 s, the width of the welding edge is 10 mm, and the thickness of the welding edge is 0.6 mm±0.1 mm.

The reasons for selecting the processing parameters and the specific welding way in S5 is similar to the specific contents in S3, and will not be repeated here.

Step S6: Using a hot-melt ring welding machine to weld the circular upper top, the cylindrical upper part, the inverted truncated cone lower part, and the circular lower bottom to obtain the single-use bioprocessing bag, wherein the hot-melt ring welding machine is used to weld the annular welding edge.

Optionally, when using the hot-melt ring welding machine to perform welding of the circular upper top, the cylindrical upper part, the inverted truncated cone lower part, and the circular lower bottom, the processing parameters are as the following: the air pressure is 0.6 MPa, the temperature of the upper mold is 135° C.±2, the welding time is 50 s~55 s, and the width of the welding edge is 10 mm. In this embodiment, the lower mold is not heated.

The reasons for selecting the processing parameters in S6 are similar to the specific contents in S3, and will not be repeated here. The specific welding way in S6 will be described in detail below in conjunction with the specific structure of the hot-melt ring welding machine.

Wherein, the sequence of steps S3, S4, and S5 is not limited in the embodiment of the present invention, and the sequence can be steps S3, S4, S5, or steps S3, S5, S4, or steps S4, S3, S5, or steps S4, S5, S3, or steps S5, S4, S3, or steps S5, S3, S4, and those skilled in the art can make selection according to actual needs.

On one hand, because during the process of manufacturing the single-use bioprocessing bag using the above manufacturing method of the single-use bioprocessing bag, at least two bag openings are welded on the first film material to obtain the circular upper top, the second film material is welded to obtain the cylindrical upper part, the third film material is welded to obtain the inverted truncated cone lower part, and the hot-melt ring welding machine is used to weld the circular upper top, the cylindrical upper part, the inverted truncated cone lower part, and the circular lower bottom, so as to obtain the single-use bioprocessing bag, there are fewer welding times, fewer welding edges, and smaller overlapping parts of the welding edges during the manufacturing process of the single-use bioprocessing bag, which can improve the physical properties of the welding edge of the single-use bioprocessing bag and reduce the risk of rupture of the single-use bioprocessing bag and the leakage of the culture liquid in the bag. On the other hand, because the first film material, the second film material, the third film material and the fourth film material are all made by cutting the raw film material according to the first cutting template, the second cutting template, the third cutting template and the fourth-cutting template that are made based on the size and shape of the bioreactor, the conformability between the single-use bioprocessing bag and the bioreactor can be improved, and the problem that the flow field shape of the culture liquid inside a culture system deviates from ideal flow field shape confirmed during design is solved, thus helping to improve the final cell culture effect.

Optionally, the manufacturing method of the single-use bioprocessing bag further comprises: during the process of using the hot-melt ring welding machine to perform welding of the circular upper top, the cylindrical upper part, the inverted truncated cone lower part, and the circular lower bottom, the upper mold and the lower mold of the hot-melt ring welding machine are changed respectively according to the diameters of the circular upper top and the diameter of the circular lower bottom.

Optionally, the manufacturing method of the single-use bioprocessing bag further comprises: after obtaining the single-use bioprocessing bag, performing an air tightness test on the single-use bioprocessing bag using a pressure drop method, to determine whether the air tightness of the single-use bioprocessing bag meets the requirements, so as to avoid to use in the bioreactor defective products produced during the manufacturing process, such as the single-use bioprocessing bag that does not meet the air tightness requirements, to cause the leakage of the culture liquid.

The operation method above is as follows. The single-use bioprocessing bag obtained by welding is fully cooled, and then its multiple bag openings are sealed with a silicone tube, and at the same time two bag openings are left for pressure-holding and leak testing. In order to be able to quickly and effectively test the integrity of the single-use bioprocessing bag, it needs to maintain a constant temperature to avoid temperature fluctuations that will affect the pressure inside the single-use bioprocessing bag and thus affect the accuracy of the test results. After the pressure holding time is over, if the actual pressure inside the single-use bioprocessing bag is 80% or more of the holding pressure (that is, the pressure inside the single-use bioprocessing bag at the beginning of the pressure holding), the air tightness of the single-use bioprocessing bag is qualified, otherwise the air tightness of the single-use bioprocessing bag is unqualified.

Optionally, in the pressure drop method above, the parameters of pressure holding process are as following. The ambient temperature is 26° C.±2° C. in summer time, or 20° C.±2° C. in winter time, humidity is 40%-60%, and the pressure holding time is 48 h. When the volume of the single-use bioprocessing bag is 5 L, the holding pressure is 4 kPa; when the volume of the single-use bioprocessing bag is 50 L, the holding pressure is 2 kPa; when the volume of the single-use bioprocessing bag is 300 L, the holding pressure is 0.6 kPa; and when the volume of the single-use bioprocessing bag is 1200 L, the holding pressure is 0.3 kPa.

In addition, the present invention also relates to a single-use bioprocessing bag, which is manufactured by using any of the above-mentioned manufacturing methods of the single-use bioprocessing bag. Specifically, as shown in FIG. 1, the single-use bioprocessing bag comprises the circular upper top 1, the cylindrical upper part 2, the inverted truncated cone lower part 3, and the circular lower bottom 4, and the circular upper top 1 has at least two bag openings 11.

Since the single-use bioprocessing bag is made by using the manufacturing method of the single-use bioprocessing bag described in any of the above embodiments, the single-use bioprocessing bag has fewer welding edges, and smaller overlapping parts of the welding edges, which can improve the physical properties of the welding edges of the single-use bioprocessing bag and reduce the risk of rupture of the single-use bioprocessing bag and the leakage of the culture liquid in the bag. And, the conformability between the single-use bioprocessing bag and the bioreactor is relatively better, which solves the problem of the flow field shape of the culture liquid inside the culture system deviating from ideal flow field shape confirmed during design, and then helps to improve the final cell culture effect.

Figure 7:
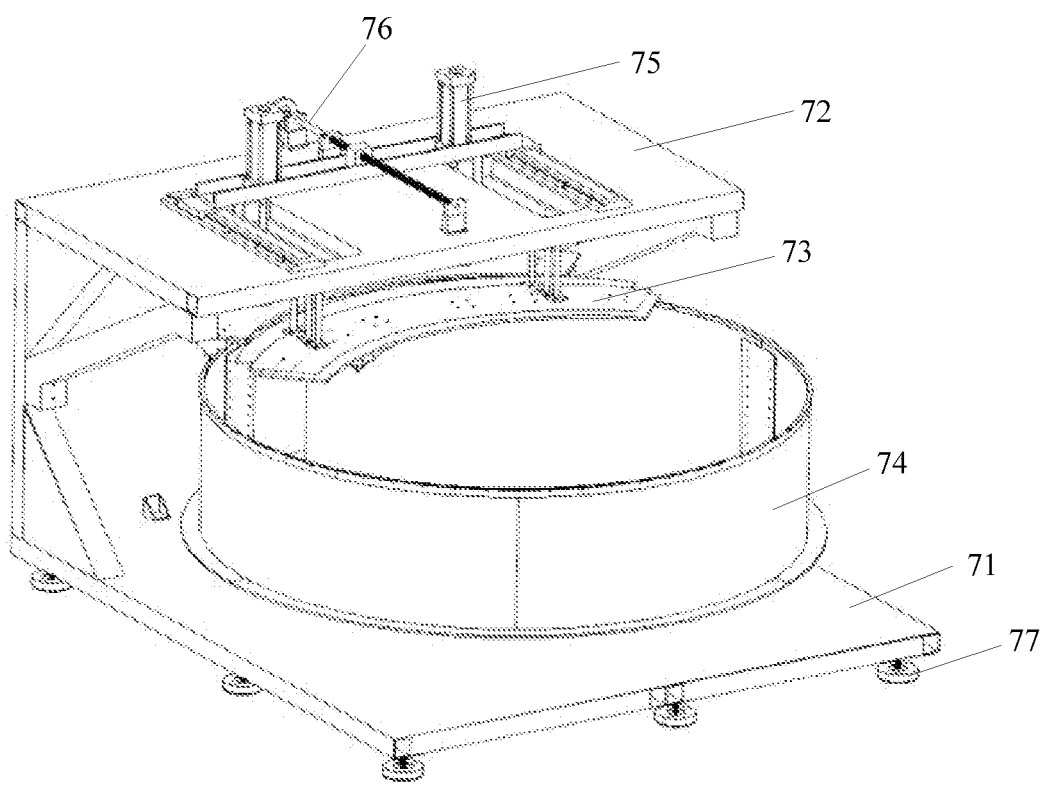
FIG. 7 shows a schematic diagram of a structure of a hot-melt ring welding machine.

In addition, the present invention also relates to a hot-melt ring welding machine. Specifically, as shown in FIG. 7, FIG. 7 is a schematic diagram of the structure of a hot-melt ring welding machine, wherein the hot-melt ring welding machine comprises a base 71, a support 72, an upper mold 73, a lower mold 74, a cylinder 75, and a screw guide rail 76. The lower mold 74 is detachably connected to the base 71, the support 72 is fixed to one end of the base 71, the screw guide rail 76 is fixed to the support 72, the cylinder 75 is fixed to the screw guide rail 76, the upper mold 73 is detachably connected to the bottom of the piston of the cylinder 75, the upper mold 73 is an arc-shaped piece, the lower mold 74 is a hollow cylinder, the upper mold 73 has a built-in heating module, and the lower mold 74 is able to rotate about its axial direction at any angle between 0 and 360°.

When using the above-mentioned hot-melt ring welding machine to weld the ring-shaped welding edges, the heating module built in the upper mold 73 of the hot-melt ring welding machine is used to heat the upper mold to a set temperature, and the upper mold 73 is given a downward pressure through the cylinder 75, which causes the upper mold 73 and the lower mold 74 to squeeze the film material at a fixed pressure for welding. During the welding process, the lower mold 74 rotates, so that the film material on the lower mold 74 rotates, making the film material corresponding to the cylinder of the hollow cylinder lower mold 74 is placed between the lower mold 74 and the upper mold 73 for a certain period of time, and then is welded, so that the ring-shaped welding edges can be welded by the hot-melt ring welding machine.

The lower mold 74 can be driven by a motor to rotate. It can rotate at a constant speed or rotate a certain angle each time. The angle is a central angle corresponding to the upper mold 73 of the arc-shaped piece. After rotation, it stays for a certain period of time for welding. It continues until the welding of ring-shaped welding edge is completed. The selection of rotation speed of constant speed rotation and the staying time should meet the following requirements: the welding time of each position of the welding edge meets the requirements of the welding time in the processing parameters of the above-mentioned step S6. Those skilled in the art can make reasonable designs based on this.

Optionally, the lower mold can rotate from 0 to 360° about its axial direction, so that the rotation of the lower mold drives the rotation of the film or structure to be welded, and thus the upper mold with a relatively smaller size can weld relatively large film material or structure, and can respectively weld various positions of irregularly shaped film material or structure, therefore helping to improve the scope of application of the hot-melt ring welding machine.

Optionally, in order to ensure that the mold and the film material of the ring-shaped welding edges are uniformly pressured, a silicone plate is laid on the upper surface of the lower mold, so that the upper mold and the lower mold are uniformly pressured to ensure the uniformity of the welding effect. The inventors found that if the silicone plate is too thin, the effect is not good, and if the silicone plate is too thick, the cost is too high. Based on this, the thickness of the silicone plate is selected as 2 mm.

Optionally, as shown in FIG. 7, the hot-melt ring welding machine comprises two cylinders 75. In the vertical direction, the position of the screw guide rail 76 overlaps with the position of the symmetry axis of the upper mold 73, and the two cylinders 75 are symmetrically arranged with respect to the symmetry axis of the upper mold 73, so that pressure is applied to the upper mold 73 by the two cylinders 75 at the same time. Thus, the pressure at each position of the upper mold 73 is relatively more uniform, the welding effect is relatively more uniform, and the physical properties of the welding edges are relatively better.

Optionally, a plurality of rollers 77 are provided at the bottom of the base 71 to facilitate the movement of the hot-melt ring welding machine.

The present invention provides a single-use bioprocessing bag and manufacturing method thereof, and a hot-melt ring welding machine. On one hand, because during the process of manufacturing the single-use bioprocessing bag using the above manufacturing method of the single-use bioprocessing bag, at least two bag openings are welded on the first film material to obtain the circular upper top, the second film material is welded to obtain the cylindrical upper part, the third film material is welded to obtain the inverted truncated cone lower part, and the hot-melt ring welding machine is used to weld the circular upper top, the cylindrical upper part, the inverted truncated cone lower part, and the circular lower bottom, so as to obtain the single-use bioprocessing bag, there are fewer welding times, fewer welding edges, and smaller overlapping parts of the welding edges during the manufacturing process of the single-use bioprocessing bag, which can improve the physical properties of the welding edge of the single-use bioprocessing bag and reduce the risk of rupture of the single-use bioprocessing bag and the leakage of the culture liquid in the bag. On the other hand, because the first film material, the second film material, the third film material and the fourth film material are all made by cutting the raw film material according to the first cutting template, the second cutting template, the third cutting template and the fourth-cutting template that are made based on the size and shape of the bioreactor, the conformability between the single-use bioprocessing bag and the bioreactor can be improved, and the problem that the flow field shape of the culture liquid inside a culture system deviates from ideal flow field shape confirmed during design is solved, thus helping to improve the final cell culture effect.

Finally, it should be noted that the above embodiments are only used to illustrate the technical solutions of the present invention, but not to limit it. Although the present invention has been described in detail with reference to the foregoing embodiments, those of ordinary skill in the art should understand it is still possible to modify the technical solutions recorded in the foregoing embodiments, or equivalently replace some or all the technical features. Such modifications or replacements do not make the essence of the corresponding technical solutions to deviate from the scope of the present invention.

The invention claimed is:

1. A manufacturing method of a single-use bioprocessing bag, wherein the single-use bioprocessing bag is used to be placed in a bioreactor, with an upper top of the bioreactor being circular, an upper part of the bioreactor being cylindrical, a lower part of the bioreactor being inverted truncated cone shape, and a lower bottom of the bioreactor being circular, the single-use bioprocessing bag comprises a circular upper top, a cylindrical upper part, a lower part of an inverted truncated cone, and a circular lower bottom, with the circular upper top having at least two bag openings;

the manufacturing method comprises:
a first cutting template, a second cutting template, a third cutting template, and a fourth cutting template being made respectively according to the upper top, the upper part, the lower part and the lower bottom of the bioreactor;
cutting a raw film material according to the first cutting template to obtain a first film material, cutting the raw film material according to the second cutting template to obtain a second film material, cutting the raw film material according to the third cutting template to obtain a third film material, cutting the raw film material according to the fourth cutting template to obtain a fourth film material, and the fourth film material directly serving as the circular lower bottom;
welding the at least two bag openings on the first film material to obtain the circular upper top;
welding the second film material to obtain the cylindrical upper part;
welding the third film material to obtain the inverted truncated cone lower part;
using a hot-melt ring welding machine to weld the circular upper top, the cylindrical upper part, the inverted truncated cone lower part, and the circular lower bottom to obtain the single-use bioprocessing bag, wherein the hot-melt ring welding machine is used to weld an annular welding edge;
wherein when welding the at least two bag openings on the first film material, a layer of high temperature cloth is placed on a non-welding surface of the first film material.

2. The manufacturing method of a single-use bioprocessing bag according to claim 1, wherein the error between the size of the first film material and the size of the first cutting template is less than or equal to 2 mm, the error between the size of the second film material and the size of the second cutting template is less than or equal to 2 mm, the error between the size of the third film material and the size of the third cutting template is less than or equal to 2 mm, and the error between the size of the fourth film material and the size of the fourth cutting template is less than or equal to 2 mm.

3. The manufacturing method of a single-use bioprocessing bag according to claim 2, wherein when cutting the raw film material, two layers of the raw film material at the most are cut each time.

4. The manufacturing method of a single-use bioprocessing bag according to claim 1, wherein when welding the at least two bag openings on the first film material, the processing parameters are as following:
the air pressure is 0.5 MPa, the temperature of the upper mold is 110° C.±2° C., the temperature of the lower mold is 80° C.±2° C., the gap between the upper mold and the lower mold is 1.5 mm, the welding time is 6 s~8 s, and the width of the welding edge is 8 mm.

5. The manufacturing method of a single-use bioprocessing bag according to claim 1, wherein when welding the second film material, the processing parameters are as following:
the air pressure is 0.6 MPa, the temperature of the upper mold is 135° C.±2° C., the temperature of the lower mold is 90° C.±2° C., the gap between the upper mold and the lower mold is 0.6 mm, the welding time is 6 s~9 s, the width of the welding edge is 10 mm, and the thickness of the welding edge is 0.6 mm±0.1 mm.

6. The manufacturing method of a single-use bioprocessing bag according to claim 1, wherein when welding the third film material, the processing parameters are as following:
the air pressure is 0.6 MPa, the temperature of the upper mold is 135° C.±2° C., the temperature of the lower mold is 90° C.±2° C., the gap between the upper mold and the lower mold is 0.6 mm, the welding time is 5 s$^{18}$ 9 s, the width of the welding edge is 10 mm, and the thickness of the welding edge is 0.6 mm±0.1 mm.

7. The manufacturing method of a single-use bioprocessing bag according to claim 1, wherein when using the hot-melt ring welding machine to perform welding of the circular upper top, the cylindrical upper part, the inverted truncated cone lower part, and the circular lower bottom, the processing parameters are as following:
the air pressure is 0.6 MPa, the temperature of the upper mold is 135° C.±2, the welding time is 50 s~55 s, and the width of the welding edge is 10 mm.

8. The manufacturing method of a single-use bioprocessing bag according to claim 1, wherein the manufacturing method further comprises: during the process of using the hot-melt ring welding machine to perform welding of the circular upper top, the cylindrical upper part, the inverted truncated cone lower part, and the circular lower bottom, the upper mold and the lower mold of the hot-melt ring welding machine are changed according to the diameter of the circular upper top and the diameter of the circular lower bottom, respectively.

9. The manufacturing method of a single-use bioprocessing bag according to claim 1, wherein the manufacturing method further comprises: after obtaining the single-use bioprocessing bag, performing an air tightness test on the single-use bioprocessing bag using a pressure drop method.

10. The manufacturing method of a single-use bioprocessing bag according to claim 9, wherein in the pressure drop method, the parameters of a pressure holding process are as following:
the ambient temperature is 26° C.±2° C. in summer time, 20° C.±2° C. in winter time, the humidity is 40%-60%, and a pressure holding time is 48 h;
when the volume of the single-use bioprocessing bag is 5 L, the holding pressure is 4 kPa;
when the volume of the single-use bioprocessing bag is 50 L, the holding pressure is 2 kPa;
when the volume of the single-use bioprocessing bag is 300 L, the holding pressure is 0.6 kPa; and
when the volume of the single-use bioprocessing bag is 1200 L, the holding pressure is 0.3 kPa.

11. A single-use bioprocessing bag, wherein the single-use bioprocessing bag is made with the manufacturing method of a single-use bioprocessing bag according to claim 1.

12. A hot-melt ring welding machine, comprising a base, a support, an upper mold, a lower mold, a cylinder, and a screw guide rail, wherein the lower mold is detachably connected to the base, the support is fixed to one end of the base, the screw guide rail is fixed on the support, the cylinder is fixed on the screw guide rail, the upper mold is detachably connected to the bottom of the piston of the cylinder, the upper mold is of an arc-shaped piece, the lower mold is a hollow cylinder, the upper mold has a built-in heating module, and the lower mold is able to rotate about its axial direction at any angle between 0 and 360°.

13. The hot-melt ring welding machine according to claim 12, wherein a silicone plate is laid on the upper surface of the lower mold.

14. The hot-melt ring welding machine according to claim 13, wherein the thickness of the silicone plate is 2 mm.

15. The hot-melt ring welding machine according to claim 12, wherein the hot-melt ring welding machine comprises two cylinders, in the vertical direction the position of the screw guide rail overlaps with the position of the symmetry axis of the upper mold, and the two cylinders are symmetrically arranged with respect to the symmetry axis of the upper mold.

16. A manufacturing method of a single-use bioprocessing bag, wherein the single-use bioprocessing bag is used to be placed in a bioreactor, with an upper top of the bioreactor being circular, an upper part of the bioreactor being cylindrical, a lower part of the bioreactor being inverted truncated cone shape, and a lower bottom of the bioreactor being circular, the single-use bioprocessing bag comprises a circular upper top, a cylindrical upper part, a lower part of an inverted truncated cone, and a circular lower bottom, with the circular upper top having at least two bag openings;

the manufacturing method comprises:

a first cutting template, a second cutting template, a third cutting template, and a fourth cutting template being made respectively according to the upper top, the upper part, the lower part and the lower bottom of the bioreactor;

cutting a raw film material according to the first cutting template to obtain a first film material, cutting the raw film material according to the second cutting template to obtain a second film material, cutting the raw film material according to the third cutting template to obtain a third film material, cutting the raw film material according to the fourth cutting template to obtain a fourth film material, and the fourth film material directly serving as the circular lower bottom;

welding the at least two bag openings on the first film material to obtain the circular upper top;

welding the second film material to obtain the cylindrical upper part;

welding the third film material to obtain the inverted truncated cone lower part;

using a hot-melt ring welding machine to weld the circular upper top, the cylindrical upper part, the inverted truncated cone lower part, and the circular lower bottom to obtain the single-use bioprocessing bag, wherein the hot-melt ring welding machine is used to weld an annular welding edge;

after obtaining the single-use bioprocessing bag, performing an air tightness test on the single-use bioprocessing bag using a pressure drop method.

* * * * *